Dec. 22, 1953 M. R. JACOBUS Plant Pat. 1,234
ROSE PLANT
Filed Dec. 29, 1952 2 Sheets-Sheet 1
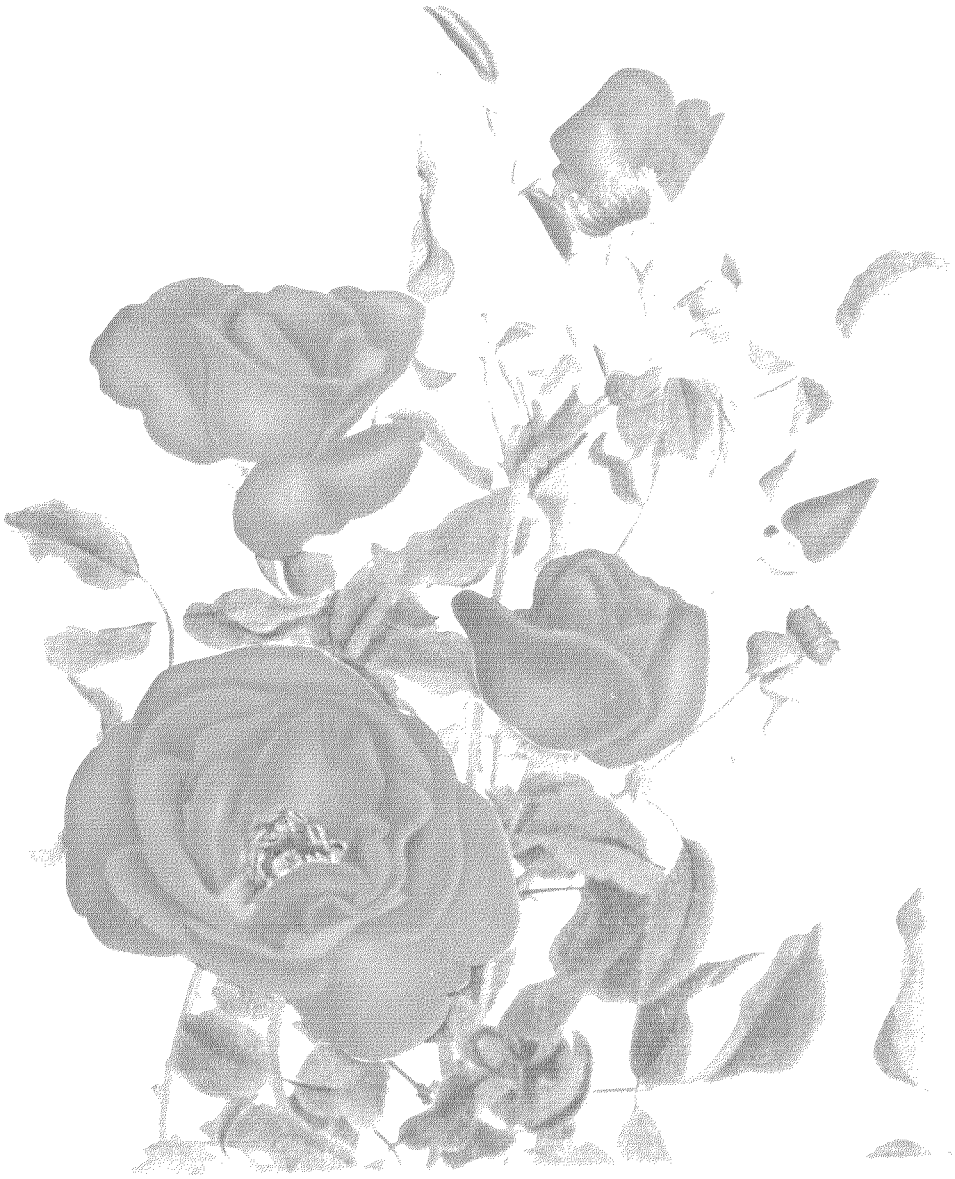
Inventor
Martin R. Jacobus
By: Robert Cobb
Attorneys Dec. 22, 1953 M. R. JACOBUS Plant Pat. 1,234
ROSE PLANT
Filed Dec. 29, 1952 2 Sheets-Sheet 2
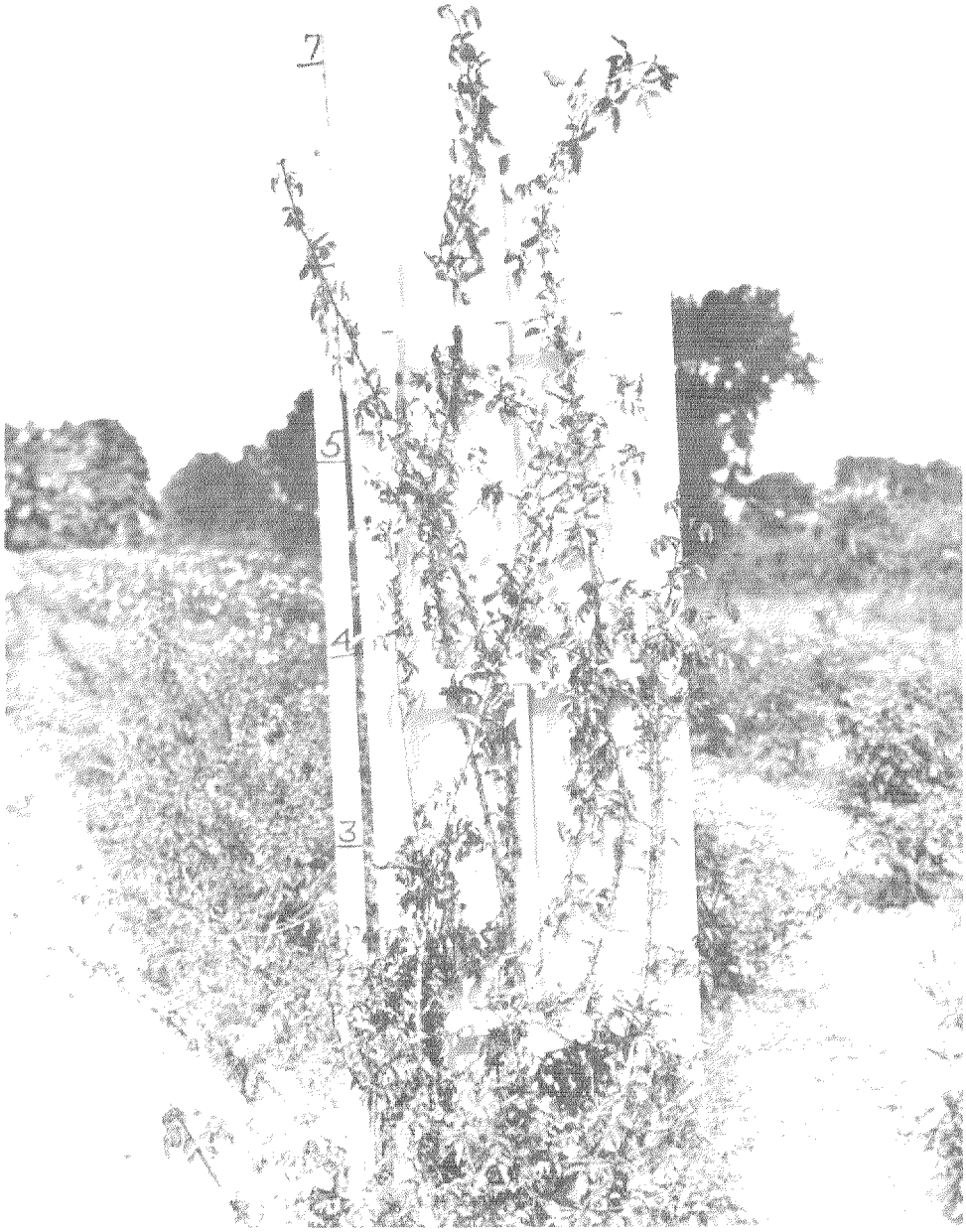
Inventor
Martin R. Jacobus
By: Robb & Robb
attorneys Patented Dec. 22, 1953

Plant Pat. 1,234

UNITED STATES PATENT OFFICE 1,234

ROSE PLANT

Martin R. Jacobus, Ridgefield, N. J., assignor to Bobbink Nurseries, Inc., East Rutherford, N. J., a corporation of New Jersey Application December 29, 1952, Serial No. 328,540

1 Claim. (Cl. 47—61)

The present invention relates to a new and distinct variety of rose plant of the hybrid Wichuraiana class, which was originated by me by crossing the variety "Dream Girl" (Plant Patent No. 643) with the variety "New World" (unpatented).

The new variety is distinguished from its parents, as well as from all other varieties of its class, by the following unique combination of outstanding characteristics:

(1) The everblooming characteristic which is the most distinctive feature of this new variety;

(2) The pleasant and penetrating fragrance of the flowers, which begins as the buds unfurl and persists until the last petal drops;

(3) The distinctive color of the flowers which may be generally described as Spectrum Red in the newly open flower, and Rose Red in the 3-days open flower, and the retention of these colors without bluing or fading under hot or humid weather conditions;

(4) The attractive and distinctive petal formation and arrangement (the blooms are not too full, but always open perfectly), and the habit of producing enough blooms on individual stems, as well as in clusters, to make attractive and long-lasting arrangements for decorative purposes;

(5) The neat and upright habit of growth of the plant, with production of branches and canes attaining a height of 6 to 8 feet at the end of the second year, while sufficient growth is made the first year after planting to insure good blooms throughout the growing season, and without diminishing the strength and vigor of the plant during the first-year blooming period; and (6) The ability of the variety to produce good crops in the nursery rows of typical blooms for cut-flower production purposes.

With further respect to the everblooming characteristic of my new variety, I have found that it blooms more freely in June, mid-summer and in October than any other red everblooming climber that has come to my attention. Its ability to produce good crops of typical blooms on 2-year old plants in the nursery rows is generally accepted by rosarians in general and by nurserymen as well, as one of the best and most certain tests for remontancy or everblooming characteristics in older and longer-established plants.

In comparison with its parent "Dream Girl," this parent variety is well-known as a pillar type climber, and is remontant, quite disease-resistant, and very floriferous. The other parent "New World" is classified as a floribunda rose, and is a strong grower. My new variety may be best compared favorably in respect to its plant habits, hardiness and growth to the well-known climber "Paul's Scarlet" (unpatented), but the color and form of the blooms of my new variety are totally different from those of "Paul's Scarlet." It will accordingly be understood from the foregoing that my new variety has combined in a new combination the most desirable and outstanding characteristics of its parents and other popular rose varieties.

Asexual reproduction of my new variety by budding at East Rutherford, New Jersey, shows that the foregoing characteristics and distinctions come true to form and are established and transmitted through succeeding propagations.

The accompanying drawings show typical specimens of my new variety, one of said drawings depicting in color several specimens of the flowers, foliage and stems in different stages of development, while the other drawing depicts in black-and-white the general characteristics and habits of growth of the plant, including the climbing characteristic which is apparent from the measuring scale marked in feet beside the plant.

The following is a detailed description of my new variety, with color terminology in accordance with Ridgway's Color Standards and Nomenclature, except where general color terms of ordinary dictionary significance are obvious:

Type: Hardy; outdoor; climber; seedling; for garden decoration and for cut-flowers.

Class: Hybrid Wichuraiana.

Breeding: Seedling.

*Seed parent.*—"Dream Girl."

*Pollen parent.*—"New World."

Propagation: Holds its distinguishing characteristics through succeeding propagations by budding.

*Flower*

Locality where grown and observed: East Rutherford, New Jersey.

Continuity: Intermittent.

Fragrance: Penetrating.

Flowers borne: Several to stem; in irregular, rounded cluster; on strong, medium length stems.

Quantity of bloom: Abundant, outdoors.

Bud:

*Peduncle.*—Medium length; medium caliper; erect; almost smooth; with a few red hairs. Color—light green.

*Before calyx breaks.*—Size—medium. Form—short; oval; with foliaceous appendages on the surface of the bud; with bristle-like foliaceous parts extending beyond the tip of the bud equal to one-half of its length. Color—Deep Dull Yellow Green, Plate XXXII, 31*k*.

*As calyx breaks.*—Color—Oxblood Red, Plate I, 1*k*.

*As first petal opens.*—Size—medium. Form—long; pointed. Color — outside: Pomegranate Purple, Plate XII, 71*i*; inside: Rose Red, Plate XII, 71.

*Opening.*—Opens up well; is retarded from opening by hot and dry weather.

Bloom:

*Size, when fully open.*—Medium; from 3 inches to 3¼ inches.

*Petalage.*—Semi-double; from 13 to 15 petals; arranged regularly.

*Form.*—Open; high center at first; becoming flat-open; petals being at first loosely rolled outward; becoming later at maturity very loosely rolled outward.

Petals: Thick; with inside velvety and outside satiny.

*Shape.*—Outside — round; scalloped; apex with 3 notches. Intermediate — round; scalloped; apex with 1 notch. Inside—round; scalloped irregularly.

This description of a newly open flower was made from a rose grown outdoors in the month of June, at East Rutherford, New Jersey:

*Color.*—Outside petal—outside surface: Spectrum Red, Plate I, 1; inside surface: Rose Red, Plate XII, 71. Intermediate petal—outside surface: Spectrum Red, Plate I, 1; inside surface: Rose Red, Plate XII, 71. Inner petal — outside surface: Spectrum Red, Plate I, 1; inside surface—Carmine, Plate I, 1*i*.

This description was made from a rose that was open for three days outdoors in the month of June, at East Rutherford, New Jersey:

*Color.*—Outside petal—outside surface: Tyrian Rose, Plate XII, 69, blended with Rose Color, Plate XII, 71*b*; inside surface: Rose Red, Plate XII, 71, blended into Rose Color, Plate XII, 71*b*. Inner petal—outside surface: Spinel Pink, Plate XXVI, 71*b*; inside surface: Rose Color, Plate XII, 71*b*.

*General color effect.*—Newly opened flower—Spectrum Red, Plate I, 1. Three days open—Rose Red, Plate XII, 71.

*Behavior.*—Drop off cleanly; fading purple.

*Flower longevity.*—On bush in garden—3 days in June. Cut roses grown outdoors kept at living-room temperatures—3 days in June.

*Reproductive organs*

Stamens: Many; arranged regularly. Color — Nopal Red, Plate I, 3*i*.

Filaments: Short; most with anther. Color—Nopal Red, Plate I, 3*i*, blending into Peach Red, Plate I, 5*b*.

Anthers: Medium size; all open at once. Color—Antimony Yellow, Plate XV, 17*b*.

Pollen: Moderate. Color—Russet, Plate XV, 13*k*.

Pistils: Few.

Styles: Very even; very short; medium caliper; columnar. Color—Base Light Viridine Yellow, Plate V, 29*b*; remainder Brazil Red, Plate V, 5*i*.

Stigma: Color—Citron Green, Plate XXXI, 25*b*.

Ovaries: All enclosed in calyx.

Hips: Short; globular; very smooth; walls fleshy. Color—Light Cress Green, Plate XXXI, 29*i* to Kildare Green, Plate XXXI, 29*b*.

Sepals: Permanent; moderately long; spear-shaped; recurved. Color—Kildare Green, Plate XXXI, 29*b*.

Seeds: Few; small.

*Plant*

Foliage:

*Leaves.*—Compound of 5 leaflets; normal abundance; moderately large; moderately heavy; glossy.

*Leaflets.*—Oval-shaped; with acute apex; round base; margins simply serrate.

*Color.*—Mature—upper surface: Jade Green, Plate XXXI, 27*k*; under surface: Rainette Green, Plate XXXI, 27*i*. Young—upper surface: Light Cress Green, Plate XXXI, 29*k*, with edges Pomegranate Purple, Plate XII, 71*i*; under surface: Neutral Red, Plate XXXVIII, 71*k* to Rainette Green, Plate XXXI, 27*i*.

*Rachis (the supporting stem of the compound leaf).* — Medium caliper. Upper side—grooved; hairy. Under side — extremely smooth.

*Stipules.* — Very short; moderately narrow; with moderately short points turning out at an angle of less than 45°.

*Disease.* — Resistant to mildew and blackspot, as determined by comparison with established plants at East Rutherford, New Jersey, and also in Northern New Jersey, planted among other climbers and hybrid teas, a number of which were highly susceptible to both mildew and blackspot, but without any evidence of either mildew or blackspot in my new variety, even without the application of fungicides.

Growth:

*Habit.*—Climbing.

*Growth.*—Vigorous.

*Canes.*—Heavy.

*Main stems.*—Color—dull bronze. Thorns—several; medium length; hooked downward; with long, narrow base. Prickles—several; color—red. Hairs—few; color—green.

*Branches.*—Color—dull green. Thorns—several; medium length; hooked downward; with long, narrow base. Prickles—several; color—reddish. Hairs—few; color—green.

*New shoots.*—Color—bright green. Thorns—few; medium lengths; hooked downward; with short, narrow base. Prickles—few; color—reddish. Hairs—few; color—green.

I claim:

A new and distinct variety of rose plant of the hybrid Wichuraiana class, substantially as herein shown and described, characterized particularly as to novelty by its everblooming habit, by the penetrating fragrance of its blooms, by its excellent petal formation and arrangement with attending perfect opening of its blooms, by the Spectrum Red to Rose Red general color tonality of its blooms and their absence of bluing or fading under hot and humid weather conditions, by its neat, upright and hardy habits of growth, by its production of good blooms throughout the growing season during the first year after planting and without diminishing the strength of the plant, by its heavy production of blooms on 2-year plants in the nursery rows, and by its good resistance to mildew and blackspot.

MARTIN R. JACOBUS.

No references cited.